United States Patent [19]
Lough et al.

[11] Patent Number: 5,900,481
[45] Date of Patent: May 4, 1999

[54] BEAD LINKERS FOR IMMOBILIZING NUCLEIC ACIDS TO SOLID SUPPORTS

[75] Inventors: David M. Lough, Hamburg, Germany; Hubert Köster, Concord, Mass.

[73] Assignee: Sequenom, Inc., San Diego, Calif.

[21] Appl. No.: 08/746,036

[22] Filed: Nov. 6, 1996

[51] Int. Cl.$^6$ .............................. C07H 1/00; C07H 21/04; C07H 33/18

[52] U.S. Cl. ...................... 536/55.3; 536/56; 536/123.1; 502/233; 525/332.2

[58] Field of Search ...................... 536/55.3, 56, 123.1; 502/233; 525/332.2

[56] References Cited

U.S. PATENT DOCUMENTS

| | | | |
|---|---|---|---|
| 4,139,346 | 2/1979 | Rabbani | 422/56 |
| 4,797,355 | 1/1989 | Stabinsky | 435/6 |
| 4,806,546 | 2/1989 | Carrico et al. | 536/27 |
| 5,242,974 | 9/1993 | Holmes | 525/54.11 |
| 5,380,833 | 1/1995 | Urdea | 536/22.1 |
| 5,512,439 | 4/1996 | Hornes et al. | 435/6 |

FOREIGN PATENT DOCUMENTS

| | | |
|---|---|---|
| 0396116 | 11/1990 | European Pat. Off. . |
| 0455905 | 11/1991 | European Pat. Off. . |
| 9306925 | 4/1993 | WIPO . |

OTHER PUBLICATIONS

Arshady, Reza; Review: Beaded Polymer Supports and Gels, I. Manufacturing Techniques; Journal of Chromatography, 586 (1991); pp. 181–197.

Arshady, Reza; Review: Beaded Polymer Supports and Gels, II. Physico–Chemical Criteria and Functionalization; Journal of Chromatography, 586 (1991); pp. 199–219.

Damha, Masad J. et al.; An Improved Procedure for Derivatization of Controlled–Pore Glass Beads for Solid–Phase Oligonucleotide Synthesis; Nucleic Acids Research vol. 18, No. 13 (1990); pp. 3813–3821.

Hayashi, Toshio et al.; Immobilization of Thiol Proteases onto Porous Poly(Vinyl Alcohol) Beads; Polymer Journal vol. 25, No. 5 (1993); pp. 489–497.

Lund, Vera et al.; Assessment of Methods for Covalent Binding of Nucleic Acids to Magnetic Beads, Dynabeads, and the Characteristics of the Bound Nucleic Acids in Hybridization Reactions; Nucleic Acids Research vol. 16, No. 22 (1988).

Pon, Richard T. et al.; Research Report: Derivatization of Controlled Pore Glass Beads for Solid Phase Oligonucleotide Synthesis; BioTechniques vol. 6, No. 8 (1988); pp. 768–770, 773–775.

*Primary Examiner*—Gary L. Kunz
*Attorney, Agent, or Firm*—Foley, Hoag & Eliot; Beth E. Arnold

[57] ABSTRACT

Novel compositions comprised of at least one bead conjugated to a solid support and further conjugated to at least one nucleic acid and preferred methods for making the novel compositions are described. As compared to "flat" surfaces, beads linked to a solid support provide an increased surface area for immobilization of nucleic acids. Furthermore, by selecting a bead with the desired functionality, a practitioner can select a functionalization chemistry for immobilizing nucleic acids, which is different from the chemistry of the solid support.

14 Claims, 4 Drawing Sheets

BEAD LINKERS FOR IMMOBILIZING NUCLEIC ACIDS TO SOLID SUPPORTS

BACKGROUND OF THE INVENTION

In the fields of molecular biology and biochemistry, as well as in the diagnosis of diseases, nucleic acid hybridization has become a powerful tool for the detection, isolation, and analysis of specific oligonucleotide sequences. Typically, such hybridization assays utilize an oligodeoxynucleotide probe that has been immobilized on a solid support; as for example in the reverse dot blot procedure (Saiki, R. K., Walsh, P. S., Levenson, C. H., and Erlich, H. A. (1989) Proc. Natl. Acad. Sci. USA 86, 6230). More recently, arrays of immobilized DNA probes attached to a solid surface have been developed for sequencing by hybridization (SBH) (Drmanac, R., Labat, I., Brukner, I., and Crkvenjakov, R. (1989) Genomics, 4, 114–128), (Strezoska, Z., Paunesku, T., Radosavljevic, D., Labat, I., Drmanac, R., and Crkvenjakov, R. (1991) Proc. Natl. Acad. Sci. USA, 88, 10089–10093). SBH uses an ordered array of immobilized oligodeoxynucleotides on a solid support. A sample of unknown DNA is applied to the array, and the hybridization pattern is observed and analyzed to produce many short bits of sequence information simultaneously. An enhanced version of SBH, termed positional SBH (PSBH), has been developed which uses duplex probes containing single-stranded 3'- or 5'- overhangs. (Broude, N. E., Sano, T., Smith, C. L., and Cantor, C. R. (1994) Proc. Natl. Acad. Sci. USA, 91, 3072–3076). It is now possible to combine a PSBH capture approach with conventional Sanger sequencing to produce sequencing ladders detectable, for example by gel electrophoresis (Fu, D., Broude, N. E., Koster, H., Smith, C. L., and Cantor, C. R. (1995) Proc. Natl. Acad. Sci. USA, 92, 10162–10166).

For the arrays utilized in these schemes, there are a number of criteria which must be met for successful performance. For example, the immobilized DNA must be stable and not desorb during hybridization, washing, or analysis. In addition, the density of the immobilized oligodeoxynucleotide must be sufficient for the ensuing analyses. However, there must be minimal non-specific binding of DNA to the surface. In addition, the immobilization process should not interfere with the ability of immobilized probes to hybridize. For the majority of applications, it is best for only one point of the DNA to be immobilized, ideally a terminus.

In recent years, a number of methods for the covalent immobilization of DNA to solid supports have been developed which attempt to meet all the criteria listed above. For example, appropriately modified DNA has been covalently attached to flat surfaces functionalized with amino acids, (Running, J. A., and Urdea, M. S. (1990) Biotechniques, 8, 276–277), (Newton, C. R., et al., (1993) Nucl. Acids. Res., 21 1155–1162.), (Nikiforov, T. T., and Rogers, Y. H. (1995) Anal. Biochem., 227, 201–209) carboxyl groups, (Zhang, Y., et al., (1991) Nucl. Acids Res., 19, 3929–3933), epoxy groups (Lamture, J. B., et al., (1994) Nucl. Acids Res. 22, 2121–2125), (Eggers, M. D., et al., (1994) BioTechniques, 17, 516–524) or amino groups (Rasmussen, S. R., et al., (1991) Anal. Biochem., 198, 138–142). Although many of these methods were quite successful for their respective applications, when used to link nucleic acids to two-dimensional (flat) supports, the density of the immobilized oligodeoxynucleotide is often insufficient for the ensuing analyses (Lamture, J. B., et al., (1994) Nucl. Acids Res. 22, 2121–2125, Eggers, M. D., et al., (1994) BioTechniques, 17, 516–524).

SUMMARY OF THE INVENTION

In one aspect, the invention features novel compositions comprised of at least one bead conjugated to a solid support and further conjugated to at least one nucleic acid. In another aspect, the invention features preferred conjugation means for making the novel compositions. In a further aspect, the invention features kits containing reagents for performing the conjugations and thereby immobilizing nucleic acids to an insoluble support via a bead linker.

As compared to "flat" surfaces, beads linked to a solid support provide an increased surface area for immobilization of nucleic acids. Furthermore, by selecting a bead with the desired functionality, a practitioner can select a functionalization chemistry for immobilizing nucleic acids, which is different from the chemistry of the solid support.

The above and further features and advantages of the instant invention will become clearer from the following Detailed Description and claims.

DETAILED DESCRIPTION OF THE INVENTION

In general, the invention relates to use of functionalized beads for the immobilization of nucleic acids, wherein the beads are stably associated with a solid support.

Figure 1:
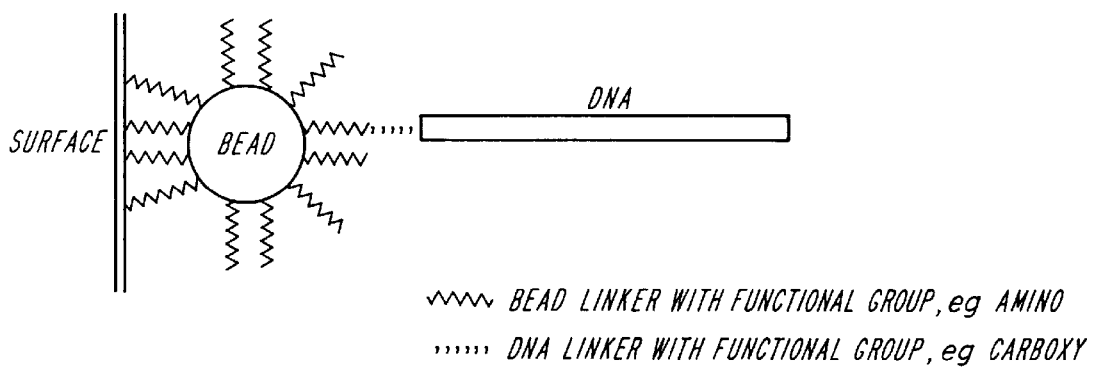
FIG. 1 is a schematic showing the covalent attachment of a bead to a solid support and DNA to the bead.
Figure 2:
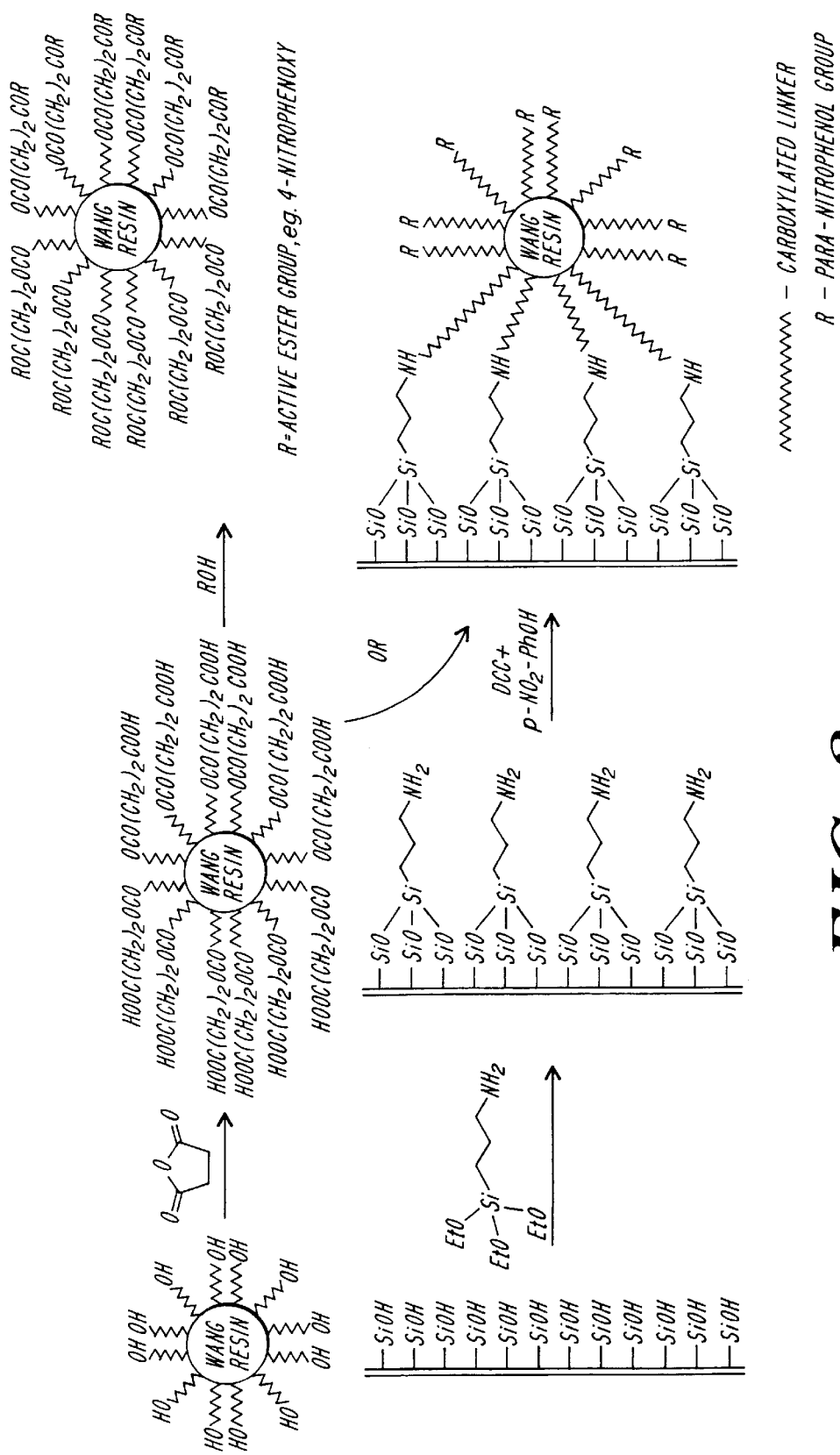
FIG. 2 is a schematic showing the covalent attachment of Wang resin beads to a solid support as described in Example 1.
Figure 3:
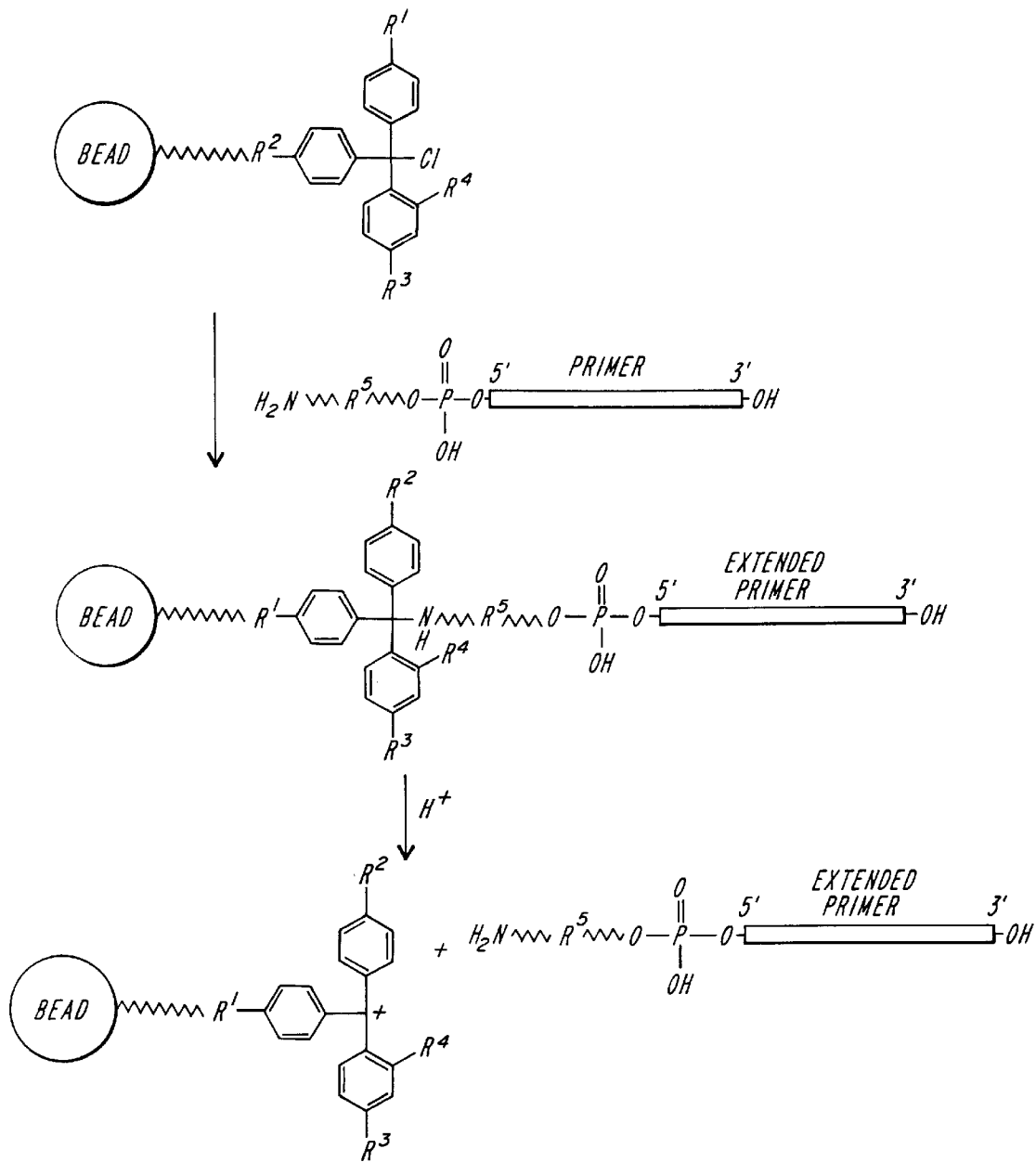
FIG. 3 is a schematic representation of nucleic acid immobilization via covalent bifunctional trityl linkers as described in Example 2.
Figure 4:
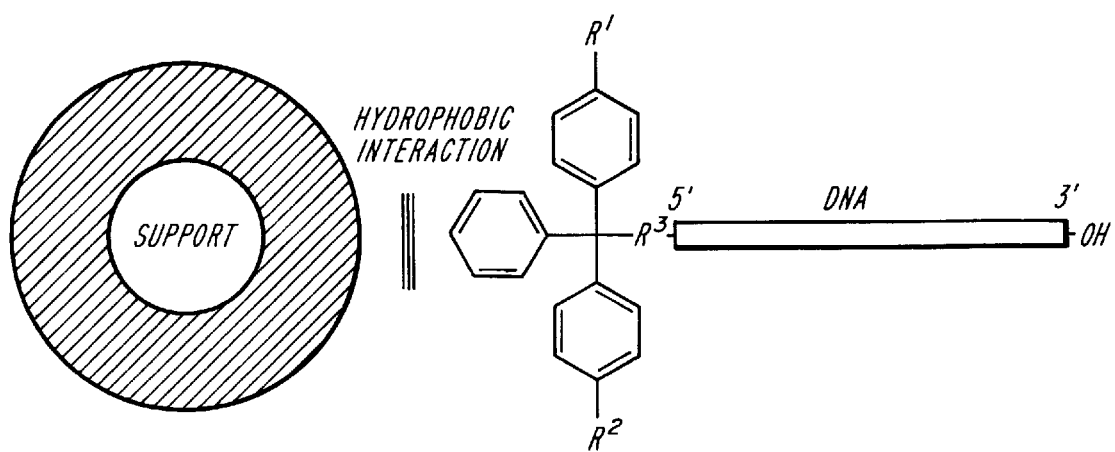
FIG. 4 is a schematic representation of nucleic acid immobilization via hydrophobic trityl linkers as described in Example 3.

FIG. 1 depicts a bead conjugated to a solid support through one or more covalent or non-covalent bonds. Nucleic acids can be immobilized on the functionalized bead before, during or after the bead is conjugated to the solid support. As used herein, the term "nucleic acid" refers to single stranded and/or double stranded polynucleotides such as deoxyribonucleic acid (DNA), and ribonucleic acid (RNA) as well as analogs or derivatives of either RNA or DNA. Also included in the term "nucleic acid" are analogs of nucleic acids such as peptide nucleic acid (PNA), phosphorothioate DNA, and the like.

Preferred nucleic acids for use in the subject invention are derivatized to contain at least one reactive moiety. Preferably the reactive moiety is at the 3' or 5' end.

Alternatively, a nucleic acid can be synthesized with a modified base. In addition, modification of the sugar moiety of a nucleotide at positions other than the 3' and 5' position is possible through conventional methods. Also, nucleic acid bases can be modified, e.g., by using N7- or N9-deazapurine nucleosides or by modification of C-5 of dT with a linker arm, e.g., as described in F. Eckstein, ed., "Oligonucleotides and Analogues: A Practical Approach," IRL Press (1991). Alternatively, backbone-modified nucleic acids (e.g., phosphoroamidate DNA) can be used so that a reactive group can be attached to the nitrogen center provided by the modified phosphate backbone.

In preferred embodiments, modification of a nucleic acid, e.g., as described above, does not substantially impair the ability of the nucleic acid or nucleic acid sequence to hybridize to its complement. Thus, any modification should preferably avoid substantially modifying the functionalities of the nucleic acid which are responsible for Watson-Crick base pairing. The nucleic acid can be modified such that a non-terminal reactive group is present, and the nucleic acid, when immobilized to the support, is capable of self-complementary base pairing to form a "hairpin" structure having a duplex region.

An appropriate "bead" for use in the instant invention includes any three dimensional structure that can be conjugated to a solid support and provides an increased surface area for binding of DNA. Preferably the bead is of a size in the range of about 1 to about 100 µm in diameter. For use in the invention, a bead can be made of virtually any insoluble or solid material. For example, the bead can be comprised of silica gel, glass (e.g. controlled-pore glass (CPG)), nylon, Wang resin, Merrifield resin, Sephadex, Sepharose, cellulose, magnetic beads, Dynabeads, a metal surface (e.g. steel, gold, silver, aluminum, silicon and copper), a plastic material (e.g., polyethylene, polypropylene, polyamide, polyester, polyvinylidenedifluoride (PVDF)) and the like. Beads can be swellable, e.g., polymeric beads such as Wang resin, or non-swellable (e.g., CPG).

Examples of insoluble supports for use in the instant invention include beads (silica gel, controlled pore glass, magnetic beads, Dynabeads, Wang resin; Merrifield resin, Sephadex/Sepharose beads, cellulose beads, etc.), capillaries, flat supports such as glass fiber filters, glass surfaces, metal surfaces (steel, gold, silver, aluminum, silicon and copper), plastic materials including multiwell plates or membranes (e.g., of polyethylene, polypropylene, polyamide, polyvinylidenedifluoride), wafers, combs, pins or needles (e.g., arrays of pins suitable for combinatorial synthesis or analysis) or beads in pits of flat surfaces such as wafers (e.g. silicon wafers), wafers with pits with or without filter bottoms.

As used herein, the term "conjugated" refers to ionic or covalent attachment. Preferred conjugation means include: streptavidin- or avidin- to biotin interaction; hydrophobic interaction; magnetic interaction (e.g. using functionalized Dynabeads); polar interactions, such as "wetting" associations between two polar surfaces or between oligo/polyethylene glycol; formation of a covalent bond, such as an amide bond, disulfide bond, thioether bond, or via crosslinking agents; and via an acid-labile linker. In a preferred embodiment for conjugating nucleic acids to beads, the conjugating means introduces a variable spacer between the beads and the nucleic acids. In another preferred embodiment, the conjugation is photocleavable (e.g. streptavidin- or avidin- to biotin interaction can be cleaved by a laser, for example for mass spectrometry).

Appropriate cross-linking agents for use in the invention include a variety of agents that are capable of reacting with a functional group present on a surface of the bead, insoluble support and or nucleic acid and with a functional group present in the nucleic acid and/ or bead, respectively. Reagents capable of such reactivity include homo- and heterobifunctional reagents, many of which are known in the art. Heterobifunctional reagents are preferred. A preferred bifunctional cross-linking agent is N-succinimidyl(4-iodoacetyl) aminobenzoate (SIAB). However, other crosslinking agents, including, without limitation, dimaleimide, dithio-bis-nitrobenzoic acid (DTNB), N-succinimidyl-S-acetyl-thioacetate (SATA), N-succinimidyl-3-(2-pyridyldithio) propionate (SPDP), succinimidyl 4-(N-maleimidomethyl)cyclohexane-1-carboxylate (SMCC) and 6-hydrazinonicotimide (HYNIC) may also be used in the novel process. In certain embodiments, the cross-linking agent can be selected to provide a selectively cleavable bond when the nucleic acid molecule is immobilized on the insoluble support. For example, a photolabile cross-linker such as 3-amino-(2-nitrophenyl)propionic acid (Brown et al. (1995) *Molecular Diversity* 4–12 and Rothschild et al (1996) *Nucleic Acids Res.* 24:351–66) can be employed to provide a means for cleaving the nucleic acid from the beads or insoluble (e.g., solid) support, if desired. For further examples of cross-linking reagents, see, e.g., S. S. Wong, "Chemistry of Protein Conjugation and Cross-Linking," CRC Press (1991), and G. T. Hermanson, "Bioconjugate Techniques," Academic Press (1995).

In one preferred embodiment, a covalent amide bond is formed between a bead and a insoluble support by reacting a carboxyl-functionalized bead with an amino-functionalized solid support (e.g., as described in Example 1, below, by reacting a carboxyl-functionalized Wang resin with an amino-functionalized silicon surface). Alternatively, a carboxyl-functionalized support can be reacted with an amino-functionalized bead, which take advantage of an acid-cleavable bifunctional trityl protection scheme employed for nucleic acid attachment. The bifunctional trityl linker can also be attached to the 4-nitrophenyl active ester on a resin (e.g. Wang resin) via an amino group as well as from a carboxy group via an amino resin.

In the bifunctional trityl approach, the beads may require treatment with a volatile acid (e.g. formic acid, trifluoracetic acid, etc.) to ensure that the nucleic acid is cleaved and can be removed. In which case, the nucleic acid may be deposited as a beadless patch at the bottom of a well in the solid support or on the flat surface of the solid support. After addition of matrix solution, the nucleic acid can then be desorbed into the mass spectrometer, for example.

The hydrophobic trityl linkers can also be exploited as acid-labile linkers by using a volatile acid or an appropriate matrix solution (e.g. a matrix solution containing, for example, 3-hydroxypicolinic acid (3-HPA) to cleave the aminolink trityl group from the nucleic acid molecule). Also, the acid lability can be changed. For example, trityl, monomethoxy, dimethoxy- or trimethoxytrityl can be changed to the appropriate p-substituted and even more acid labile tritylamine derivatives of the nucleic acids (i.e. trityl ether and tritylamine bonds to the nucleic acid can be made). Therefore, the nucleic acid may be removed from the hydrophobic linker, for example, by disrupting the hydrophobic attraction or by cleaving tritylether or tritylamine bonds under acidic or the usual mass spectrometry conditions (e.g. wherein the matrix, such as 3-HPA acts as an acid).

As pointed out above, the bead can also be associated with the solid support by non-covalent interactions. For example, a magnetic bead (e.g., a bead capable of being magnetized, e.g., a ferromagnetic bead) can be attracted to a magnetic solid support, and can be released from the support by removal of the magnetic field. Alternatively, the bead can be provided with an ionic or hydrophobic moiety, which can associate with, respectively, an ionic or hydrophobic moiety of the solid support. Also, a bead can be provided with a member of a specific binding pair, and become immobilized to a solid support provided with a complementary binding moiety. For example, a bead coated with avidin or streptavidin can be bound to a surface coated with biotin or derivatives of biotin such as imino-biotin. It will be appreciated that the binding members can be reversed, e.g., a biotin-coated bead can bind to a streptavidin-coated solid support. Other specific binding pairs contemplated for use in the invention include hormone-receptor, enzyme-substrate, nucleic acid-complementary nucleic acid, antibody-antigen and the like.

In a particularly preferred embodiment the bead is conjugated to the solid support and/or the nucleic acid is conjugated to the bead using an acid-labile bond. For example, use of a trityl linker, as further described in the following Examples 2 and 3, can provide a covalent or hydrophobic conjugation. Regardless of the nature of the conjugation, the trityl group is readily cleaved in acidic conditions.

A nucleic acid can be bound to a bead which is itself bound to a solid support, e.g., by any of the chemistries discussed above for the attachment of nucleic acids to solid supports, or attachment of beads to solid supports.

In certain embodiments, the invention contemplates the use of orthogonally-cleavable linkers for binding the bead to the solid support, and for binding the nucleic acid to the bead. Thus, a bead can be selectively cleaved from the surface without cleaving the nucleic acid from the bead, while the nucleic acid is cleaved from the bead at a later stage. For example, a disulfide linker (which can be cleaved, using, e.g., DTT) could be employed to bind the bead to the solid surface, and a bead-nucleic acid linker involving an acid-cleavable bifunctional trityl group could be used to immobilize a nucleic acid to the bead. Alternatively the linkage of the nucleic acid could be cleaved while the linkage of the bead to the support remains intact.

A bead can be bound to a solid support through a linking group which can be selected to have a length and a chemical nature such that high-density binding of beads to the solid support, and/or high-density binding of nucleic acid to the beads, is promoted. Such a linking group would have a "tree-like" structure in providing a multiplicity of functional groups per attachment site on the solid support such as polylysine, polyglutamic acid, pentaerythrole and tris-hydroxy-aminomethane.

In certain embodiments, beads can be cross-linked to other beads, e.g., by use of homobifunctional crosslinking reagents. Cross-linked beads can provide additional mechanical strength compared to non-crosslinked beads.

Once immobilized, the nucleic acids can be analyzed by any of a variety of means including, for example, spectrometric techniques such as UV/VIS, IR, fluorescence, chemiluminescence, or NMR spectroscopy, mass spectrometry, or other methods known in the art, or combinations thereof. Preferred mass spectrometer formats include ionization (I) techniques, such as matrix assisted laser desorption (MALDI), continuous or pulsed electrospray (ESI) and related methods (e.g. Ionspray or Thermospray), or massive cluster impact (MCI); these ion sources can be matched with detection formats including linear or non-linear reflectron time-of-flight (TOF), single or multiple quadrupole, single or multiple magnetic sector, Fourier Transform ion cyclotron resonance (FTICR), ion trap, and combinations thereof (e.g., ion-trap/time-of-flight). For ionization, numerous matrix/wavelength combinations (MALDI) or solvent combinations (ESI) can be employed.

The methods of the invention are useful for providing spatially-addressable arrays of nucleic acids immobilized on beads, which are further attached to solid supports. Such spatially addressable or pre-addressable arrays are useful in a variety of processes (e.g., SBH, quality control, and DNA sequencing diagnostics). In another aspect, the invention provides combinatorial libraries of immobilized nucleic acids bound to beads, which are further bound to a solid support as described above.

In still another aspect, the invention provides a kit for immobilizing nucleic acids on beads, which are further bound to a solid support. In one embodiment, the kit comprises an appropriate amount of: i) beads and ii) conjugation means. The kits described herein can also optionally include appropriate buffers; containers for holding the reagents; and/or instructions for use.

The present invention is further illustrated by the following Examples, which are intended merely to further illustrate and should not be construed as limiting. The entire contents of all of the references (including literature references, issued patents, published patent applications, and co-pending patent applications) cited throughout this application are hereby expressly incorporated by reference.

EXAMPLE 1

Attachment of Resin Beads to a Silicon Surface

A silicon surface (e.g. of a silicon wafer) is derivatized with amino groups by treatment with 3-aminopropyltriethoxysilane. Wang resin beads are treated with succinic anhydride to provide carboxyl-functionalized resin beads. The carboxyl-functionalized resin beads are then coupled to the amino-functionalized silicon surface with a coupling reagent (for example, dicyclohexylcarbodiimide (DCC)), in the presence of p-nitrophenol. The resin beads become covalently linked to the silicon surface, and the unreacted carboxyl groups of the resin are converted to the p-nitrophenyl ester (an activated ester suitable for coupling with a nucleic acid).

Alternatively, the carboxyl groups of the Wang resin are transformed to the p- nitrophenyl active esters prior to reacting with the amino-functionalized silicon surface.

Thus, resin beads can be rapidly and conveniently attached to a silicon surface, and can be simultaneously converted to a reactive form suitable for covalent attachment of nucleic acids.

EXAMPLE 2

Immobilization of Nucleic Acids on Solid Supports via an Acid-labile Covalent Bifunctional Trityl Linker Aminolink DNA was prepared and purified according to standard methods. A portion (10 eq) was evaporated to dryness on a speedvac and suspended in anhydrous DMF/pyridine (9:1; 0.1 ml). To this was added the chlorotrityl chloride resin (1 eq, 1.05 $\mu$mol/mg loading) and the mixture was shaken for 24 hours. The loading was checked by taking a sample of the resin, detritylating this using 80% AcOH, and measuring the absorbance at 260 nm. Loading was ca. 150 pmol/mg resin.

In 80% acetic acid, the half-life of cleavage was found to be substantially less than 5 minutes--this compares with trityl ether-based approaches of half-lives of 105 and 39 minutes for para and meta substituted bifunctional dimethoxytrityl linkers respectively. Preliminary results have also indicated that the 3-hydroxy picolinic acid matrix alone is sufficient to cleave the DNA from the chlorotrityl resin during MALDI mass spectrometry.

EXAMPLE 3

Immobilization of Nucleic Acids on Solid Supports via Hydrophobic Trityl Linker

The primer contained a 5'-dimethoxytrityl group attached using routine trityl-on DNA synthesis.

C18 beads from an oligo purification cartridge (0.2 mg) placed in a filter tip was washed with acetonitrile, then the solution of DNA (50 ng in 25 µl) was flushed through. This was then washed with 5% acetonitrile in ammonium citrate buffer (70 mM, 250 µl). To remove the DNA from the C18, the beads were washed with 40% acetonitrile in water (10 µL) and concentrated to ca 2 µl on the Speedvac or directly subjected to MALDI mass spectrometry.

Alternatively C18 beads were first covalently attached to a silicon surface (e.g. a silicon wafer) or adsorbed to a flat surface by hydrophobic interaction.

The results showed that acetonitrile/water at levels of ca.>30% are enough to dissociate the hydrophobic interaction. Since the matrix used in MALDI contains 50% acetonitrile, the DNA can be released from the support and MALDIed successfully (with the trityl group removed during the MALDI process).

EXAMPLE 4

Attaching Beads to Silicon Chips

Amino derivatisation of silicon surface

The silicon wafers were washed with ethanol to remove surface debris and flamed over a bunsen burner until "red hot" to ensure oxidation of the surface. After cooling, the wafers were immersed in an anhydrous solution of 3-aminopropyltriethoxysilane in toluene (25%v/v) for 3 hours. The wafers were then washed with toluene (three times) then anhydrous dimethylacetamide (three times).

Activation of Wang resin beads

Vacuum-dried Wang resin beads (5 g, 0.84 mmol/g loading, 4.2 mmol, diameter 100–200 mesh), obtained from Novabiochem, were suspended in pyridine (40 ml) with DMAP (0.1 eq, 0.42 mmol, 51 mg). To this was added succinic anhydride (5 eq, 21 mmol, 2.10 g) and the reaction was shaken for 12 hours at room temperature. After this time, the beads were washed with dimethylformamide (three times), then pyridine (three times) and suspended in pyridine/dimethylformamide (1:1, 20 ml). 4-Nitrophenol (2 eq, 8.4 mmol, 1.40 g) was added and the condensation was activated by adding dicyclohexylcarbodiimide (DCC) (2 eq, 8.4 mmol, 1.73 g) and the reaction mixture was shaken for 12 hours. The beads were then washed with dimethylformamide, pyridine and hexane, and stored at 4° C.

Coupling of Beads to Silicon Wafers

The amino-derivatised silicon wafer is treated with a suspension of the 4-nitrophenol beads in dimethyl acetamide (DMA), and within five minutes, the beads are covalently linked to the surface. The coated surface can then be washed with DMA, ethanol and water, under which conditions the beads remain as a uniform monolayer. Care must be taken to avoid scratching the beaded surface. The beads can then be reacted with the amino-functionalised modified DNA.

Equivalents

Those skilled in the art will recognize, or be able to ascertain using no more than routine experimentation, numerous equivalents to the specific procedures described herein. Such equivalents are considered to be within the scope of this invention and are covered by the following claims.

We claim:

1. A composition comprising a bead conjugated to a solid support and further conjugated to a nucleic acid.

2. A composition of claim 1, wherein the bead is made from a material selected from the group consisting of: silica gel, glass, magnet, Wang resin, Merrifield resin, metal, plastic, cellulose, Sephadex, and Sepharose.

3. A composition of claim 1, wherein the bead is swellable.

4. A composition of claim 1, wherein the bead is non-swellable.

5. A composition of claim 1, wherein the bead is in the range of 1 to 100 µm in diameter.

6. A composition of claim 1, wherein the solid support is selected from the group consisting of: beads, capillaries, plates, membranes, wafers, combs, pins, wafers and wafers with pits.

7. A composition of claim 1, wherein the nucleic acid is DNA.

8. A composition of claim 1, wherein the nucleic acid is RNA.

9. A process of making a bead conjugated to a solid support and further conjugated to a nucleic acid, comprising the steps of conjugating a bead to a nucleic acid; and conjugating a bead to a solid support.

10. A process of claim 9, wherein the bead is functionalized.

11. A process of claim 10, wherein the bead is functionalized with carboxy functional groups.

12. A process of claim 10, wherein the bead is functionalized with amino functional groups.

13. A process of claim 10, wherein the bead is conjugated to the nucleic acid prior to conjugation of the bead to the solid support.

14. A process of claim 10, wherein the bead is conjugated to the nucleic acid after the bead is conjugated to the solid support.

* * * * *

UNITED STATES PATENT AND TRADEMARK OFFICE
CERTIFICATE OF CORRECTION

PATENT NO.    : 5,900,481
DATED         : May 4, 1999
INVENTOR(S)   : Lough et al.

It is certified that error appears in the above-identified patent and that said Letters Patent is hereby corrected as shown below:

Column 2,
Line 25, please replace "Wang resin beads" with -- --Wang resin (4-(hydroxymethyl) phenoxymethylcopoly(styrene– 1% divinylbenzene(DVB) resin) beads --;

Column 3,
Line 18, please replace "Merrifield resin" with -- Merrifield resin, which is chloromethylated copolystyrene–divinylbenzene(DVB) resin --; and please replace "Sephadex, Sepharose," with -- dextran cross–linked with epichlorohydrin (e.g., Sephadex$^R$), agarose (e.g., Sepharose$^R$), --;
Line 19, please replace "Dynabeads" with -- biomagnetic separation beads such as Dynabeads$^R$, --;
Line 27, please replace "Dynabeads" with -- Dynabeads$^R$ --;
Line 28, please replace "Sephadex/Sepharose" with -- Sephadex$^R$/Sepharose$^R$ --;
Line 42, please replace "Dynabeads" with -- Dynabeads$^R$ --;

Claim 2,
Should read as the following:

2. A composition of claim 1, wherein the bead is made from a material selected from the group consisting of: silica gel, glass, magnet, 4-(hydroxymethyl)phenoxymethylcopoly(styrene– 1% divinylbenzene) resin, chloromethylated copolystyrene–divinylbenzene resin, metal, plastic, cellulose, dextran cross–linked with epichlorohydrin and agarose.

Signed and Sealed this

First Day of January, 2002

Attest:

Attesting Officer

JAMES E. ROGAN
Director of the United States Patent and Trademark Office